US010321847B2

(12) United States Patent
Maleke et al.

(10) Patent No.: US 10,321,847 B2
(45) Date of Patent: Jun. 18, 2019

(54) INTEGRATED TRACKING SYSTEM FOR ENDOCAVITY IMAGING

(71) Applicant: Siemens Medical Solutions USA, Inc., Malvern, PA (US)

(72) Inventors: Caroline Maleke, Bellevue, WA (US); Chi Hyung Seo, Sammamish, WA (US); Andrzej Milkowski, Issaquah, WA (US); John Benson, Issaquah, WA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 156 days.

(21) Appl. No.: 14/586,731

(22) Filed: Dec. 30, 2014

(65) Prior Publication Data

US 2016/0183767 A1 Jun. 30, 2016

(51) Int. Cl.
*A61B 8/12* (2006.01)
*A61B 17/00* (2006.01)
*A61B 5/06* (2006.01)
*A61B 17/34* (2006.01)
*A61B 8/00* (2006.01)
*A61B 8/08* (2006.01)
*A61B 8/06* (2006.01)
*B06B 1/02* (2006.01)

(52) U.S. Cl.
CPC .............. *A61B 5/062* (2013.01); *A61B 8/12* (2013.01); *A61B 8/4254* (2013.01); *A61B 8/445* (2013.01); *A61B 8/4461* (2013.01); *A61B 8/4483* (2013.01); *A61B 8/483* (2013.01); *A61B 17/3403* (2013.01); *A61B 8/06* (2013.01); *A61B 8/4494* (2013.01); *A61B 8/488* (2013.01); *A61B 8/5207* (2013.01); *A61B 2017/00274* (2013.01); *A61B 2017/3413* (2013.01); *B06B 1/0292* (2013.01)

(58) Field of Classification Search
CPC .................................................. A61B 8/4254
See application file for complete search history.

(56) References Cited

U.S. PATENT DOCUMENTS 5,052,396 A * 10/1991 Wedel ................ A61B 1/00142
600/461
5,623,931 A * 4/1997 Wung ................ A61B 17/3403
600/461
5,758,650 A 6/1998 Miller et al.
6,277,066 B1 8/2001 Irwin
(Continued)

OTHER PUBLICATIONS

Dima Raskolnikov et al., "Current Ability of Multiparametric Prostate Magnetic Resonance Imaging and Targeted Biopsy to Improve the Detection of Prostate Cancer", Urology Practice, 2014, pp. 13-21, vol. 1.
(Continued)

*Primary Examiner* — Tse W Chen
*Assistant Examiner* — Jason M Ip

(57) ABSTRACT

To accurately generate the three-dimensional ultrasound data and/or determine the position of the ultrasound scan relative to pre-operative data, a tracking sensor is releasably connected with the ultrasound probe. The connection positions the tracking sensor near a distal end of the probe for insertion into the patient. A needle guide may be similarly releasably connected with the probe and, at least in part, inserted into the patient.

19 Claims, 3 Drawing Sheets

(56) References Cited

U.S. PATENT DOCUMENTS

| | | | |
|---|---|---|---|
| 6,368,280 B1 | 4/2002 | Cermak et al. | |
| 6,884,219 B1 * | 4/2005 | Pruter | A61B 8/0833 600/459 |
| 7,635,336 B1 | 12/2009 | Pruter | |
| 7,959,573 B2 | 6/2011 | Furia | |
| 2001/0003790 A1 * | 6/2001 | Ben-Haim | A61B 5/0422 600/424 |
| 2009/0275833 A1 * | 11/2009 | Ikeda | A61B 8/0833 600/443 |
| 2012/0190987 A1 * | 7/2012 | Hyoun | A61B 10/0233 600/461 |

OTHER PUBLICATIONS

Disposable Endocavity Needle Guide, CIVCO Medical Solutions, 2013, 2 pages.

J. Kruecker et al., "Fusion of Transrectal Ultrasound with Pre-Acquired MRI for Prostate Biopsy Guidance", MedicaMundi, 2007-2008, pp. 24-31, vol. 52, No. 1.

Reference Guide: Tracking Bracket, for Use with GE Healthcare Volume Navigation Transducers, CIVCO Medical Solutions, 2013, 64 pages.

Volume Navigation Tracking Bracket, CIVCO Medical Solutions, 2013, 2 pages.

* cited by examiner

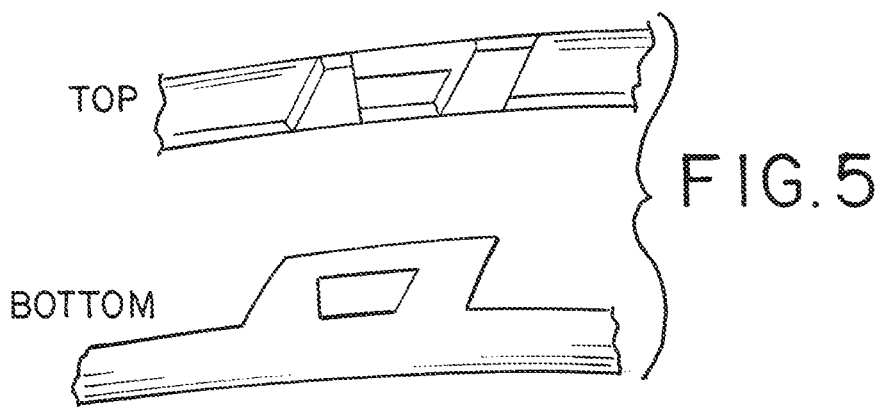
FIG. 5
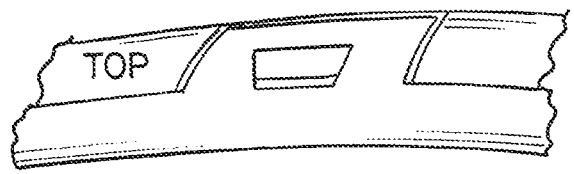
FIG. 6
FIG. 7
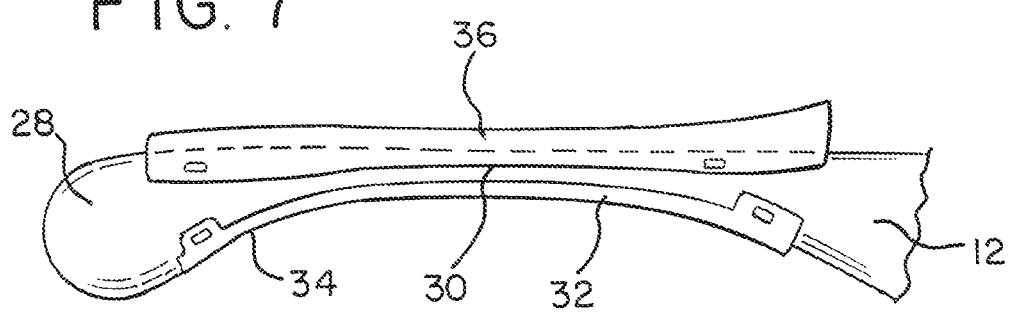

INTEGRATED TRACKING SYSTEM FOR ENDOCAVITY IMAGING

BACKGROUND

The present embodiments relate to ultrasound imaging. In particular, imaging is provided during a biopsy.

Recent technology development in fusion imaging delivers important clinical advantages, mainly in the field of magnetic resonance (MR) imaging and ultrasound imaging for prostate biopsy. Pre-operative MR data is used for biopsy planning and detail. During a biopsy, an ultrasound probe is inserted into the patient, and ultrasound is used to image the prostate and place the biopsy needle. The ultrasound scan is a two-dimensional scan, allowing fusion of the ultrasound data and the pre-operative MR data (e.g., multi-parametric MRI images, 3D MRI images). The physician may view images from the fusion to guide the biopsy. The fusion biopsy technique targets smaller abnormalities shown by MR imaging and lesions in tough areas like the anterior of the prostate and the apex. However, managing both the ultrasound probe and performing biopsy accurately may be difficult.

BRIEF SUMMARY

By way of introduction, the preferred embodiments described below include methods, transducer systems, tracking systems, and systems for ultrasound imaging during biopsy. To accurately generate the three-dimensional ultrasound data from two-dimensional ultrasound planes and/or determine the position of the ultrasound scan relative to pre-operative data, a tracking sensor is releasably connected with the ultrasound probe. The connection positions the tracking sensor near a distal end of the probe for insertion into the patient. A needle guide may be similarly releasably connected with the probe and, at least in part, inserted into the patient.

In a first aspect, an integrated needle guide tracking system is provided. An endoscopic ultrasound transducer has a distal tip opposite a handle. A tracking sensor is positioned on or adjacent to the distal tip such that the sensor is insertable within a patient cavity with the distal tip. A needle guide connects with the endoscopic ultrasound transducer.

In a second aspect, an ultrasound transducer system is provided. An ultrasound probe has a portion shaped for insertion into a patient. A housing separate from the ultrasound probe is releasably connectable with the portion. A tracking sensor is in or on the housing.

In a third aspect, a method is provided for ultrasound imaging, A tracking sensor is snapped onto an exterior of an ultrasound transducer adjacent to a distal end of the ultrasound transducer. The tracking sensor and ultrasound transducer are covered with a sterile sheath. A portion of the ultrasound transducer and the tracking sensor are inserted into a patient. An image is generated from scan data acquired with the ultrasound transducer while inserted in the patient and as a function of tracking data from the tracking sensor while inserted in the patient.

The present embodiments are defined by the following claims, and nothing in this section should be taken as a limitation on those claims. Any one or combinations of any two or more of the aspects discussed above may be used. Further aspects and advantages of the invention are discussed below in conjunction with the preferred embodiments.

BRIEF DESCRIPTION OF SEVERAL VIEWS OF THE DRAWINGS

The components and the figures are not necessarily to scale, emphasis instead being placed upon illustrating the principles of the invention. Moreover, in the figures, like reference numerals designate corresponding parts throughout the different views.

FIG. 5 shows one embodiment of mating parts in a snap arrangement, and FIG. 6 shows an example of the mating of the parts;

FIG. 7 is a side view of one embodiment of an endocavity ultrasound probe with fitted needle guide and tracking sensor;

DETAILED DESCRIPTION OF THE PREFERRED EMBODIMENTS

In order to improve the accuracy and the efficiency of the fusion biopsy procedure for prostate, an apparatus for guiding the needle while maintaining accurate position of the imaging probe is provided. The apparatus assists during image fusion and during needle placement in the biopsy procedure. A sensor bracket and/or a needle guide, which may be used simultaneously or separately, releasably attach to the imaging probe.

Figure 1:
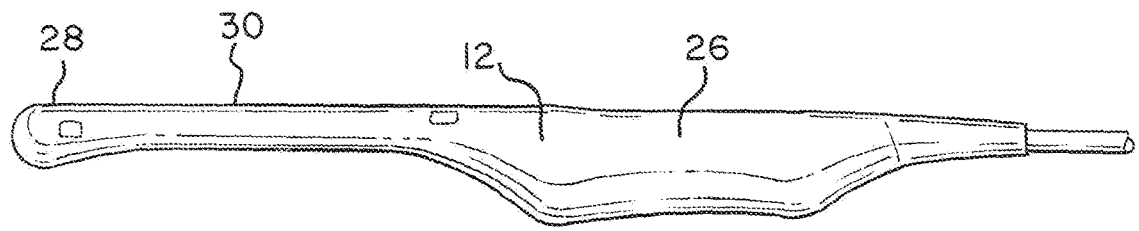
FIG. 1 illustrates an example endocavity ultrasound probe.

FIG. 1 shows one embodiment of an ultrasound probe 12. The ultrasound probe 12 of the example of FIG. 1 is an endocavity probe or endoscopic ultrasound transducer, such as sized and/or shaped for prostate ultrasound scanning. The endocavity probe is sized and/or shaped for insertion into the patient, such as insertion within a rectum of a patient. Other endocavity probes have other shapes, such as being designed for insertion into other cavities or within the patient. For example, a transeshopegeal probe, transvaginal probe, OB/GYN probe, or catheter probe is used. Other probes for insertion into the patient may be used, such as an intra-operative probe.

The ultrasound probe 12 has a portion for insertion into the patient. The portion includes a distal tip opposite a handle 26. The handle 26 is sized and shaped for holding by a person. The distal tip includes an acoustic window, such as a plastic window, against which an ultrasound transducer array is positioned. The array is within a housing forming the exterior of the ultrasound probe 12. The portion of the housing for insertion into the patient includes a bulb shape part 28 at the distal end connected to the handle by an elongated cylindrical (shaft) part 30. The bulb shape part 28 has a greater circumference in axial cross section than the elongated cylindrical part 30 to provide room of the transducer array. Other shapes with different relative sizes may be used, such as not having the bulb shaped part 28 where the array fits within an end of the elongated cylinder part 30. Any of various possible shapes and/or sizes may be used.

FIGS. 2-4 and 7 show the ultrasound probe 12 used as part of an ultrasound system. The ultrasound system includes a tracking sensor 34 with an elongated housing 32 and a needle guide 36. Where the needle guide 36 is provided, an integrated needle guide tracking system is provided. Additional, different, or fewer components may be provided. For example, the tracking sensor 34 and housing 32 are used without the needle guide 36. As another example, a sterile sheath 38 is provided.

The tracking sensor 34 is a magnetic position sensor. One or more coils, such as three orthogonal coils, are used to sense orientation. An external source generates a magnetic field. Electrical signals generated on the coils of the tracking sensor 34 are used to determine the position and/or orientation of the tracking sensor 34. A wire extends from the tracking sensor 34 to a processor or other detector for indicating the absolute position and/or orientation or a relative position and/or orientation. In other embodiments, ultrasound (e.g., echo location), gyroscopes, accelerometers, camera and optical target, or other sensors for determining position and/or orientation over time are used.

The tracking sensor 34 is positioned to be closer to the distal part than a proximal part of the ultrasound probe 12. For example, the tracking sensor 34 is positioned to be on, against, or adjacent to (e.g., separated only by the housing with or without an air gap) the bulb shape part 28 of the ultrasound probe 12. This positioning places the tracking sensor 34 near the ultrasound array, so may provide more accurate position and/or orientation information of the scan plane or region of the array. In other embodiments, the tracking sensor 34 is positioned along the elongated cylindrical part 30 of the ultrasound probe 12, such as spaced closer to a middle of the cylindrical part 30 than the distal end. The tracking sensor 34 is positioned relative to the ultrasound probe 12 so that the tracking sensor 34 is within the patient during endocavity imaging. In other embodiments, the tracking sensor 34 is positioned on an exterior part of the ultrasound probe 12 during use, such as the handle.

The tracking sensor 34 has a housing 32. The tracking sensor 34 is positioned in or on the housing 32. The tracking sensor 34 is at any location in the housing 32, such as encased on an end for placement adjacent to the bulb shape part 28 or distal end. The housing 32 is a sensor bracket with the tracking sensor 34 embedded therein so that the tracking sensor 34 is inserted within the patient cavity during ultrasound scanning.

The housing 32 is plastic, resin, PEBAX® or other material. The material is light weight to avoid straining the sonographer.

Figure 2:
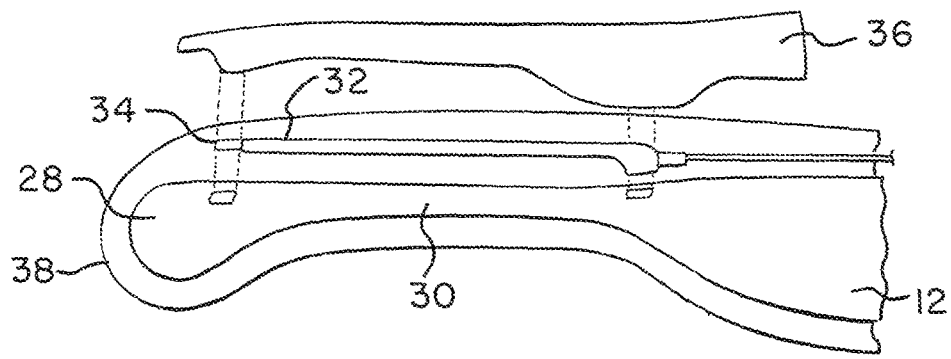
FIG. 2 is a side view of one embodiment of an ultrasound transducer system with a tracking sensor housing and needle guide.
Figure 3:
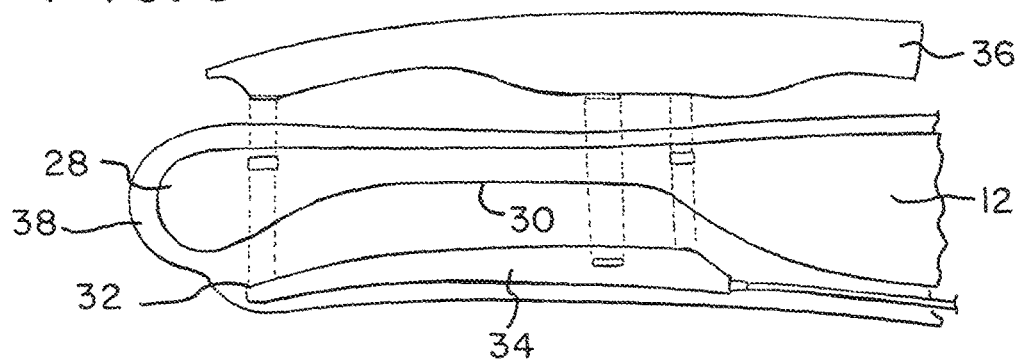
FIG. 3 is a side view of another embodiment of an ultrasound transducer system with a tracking sensor housing and needle guide.

The housing 32 has any shape and size. In one embodiment, the housing 32 has an elongated shape, such as being long and thin with no sharp edges. The housing 32 is shaped for insertion within the patient. The shape may mate with or match the contour of the ultrasound probe 12. For example, the housing 32 is curved to fit the ultrasound probe 12 along one or more dimensions, such as being generally concave orthogonal to an axial length to mate with the convex or round shape of the ultrasound probe 12 along the length and being generally convex along the axial length to mate with the concave shape of the ultrasound probe 12. FIG. 3 shows the housing 32 shaped to mate with the bulb shape part 28, along the cylindrical part 30 and a portion of the handle 26. FIG. 2 shows the housing 32 having a flat shape along the axial or length dimension to mate with the flat shape of the top of the ultrasound probe 12.

In one embodiment, the elongated housing 32 for the tracking sensor 34 is connectable to a lesser diameter portion of the bulb shape part 28 so as not to increase the greatest diameter of the ultrasound probe 12. The bulb shape part 28 has the greatest diameter that passes into the patient, and the housing 32 fits against the cylindrical part 30 behind the bulb shape part 28 so that the housing 32 does not cause a diameter with the ultrasound probe 12 greater than the diameter of the bulb shape part 28. For example, the greatest diameter of the bulb shape part 28 is 20 mm. The housing 32 as mated to the ultrasound probe 12 does not cause any diameter along the length axis to be greater than 20 mm. In other embodiments, the housing 32 causes an increase in diameter, requiring a larger hole in the patient, but has a flat or smooth surface to avoid tearing tissue of the patient.

Figure 4:
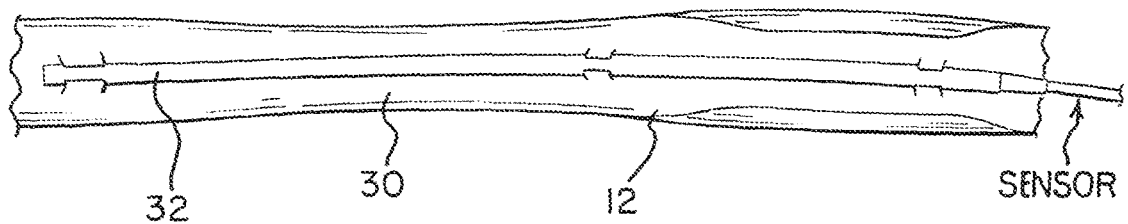
FIG. 4 is a bottom view of one embodiment of an ultrasound probe with a snap fit and releasable tracking sensor.

The housing 32 releasably connects with the ultrasound probe 12. The housing 32 is a separate part that may be connected and disconnected by a sonographer for use with different ultrasound probes 12, for cleaning, for replacement, for storage, or for other reasons. In one embodiment, the releasable connection allows for connecting and disconnecting without a tool. For example, a snap fit with easy-release is used. FIG. 5 shows a tab and post system where the tab mates with the post for snap fit. FIG. 6 shows the tab and post mated. The tab may flex to snap onto the post. A ridge in a side edge of the tab may be provided for removing the tab from the post. Other snap fits may be used. For example, FIG. 4 shows opposing tabs on the ultrasound probe 12 between which the housing 32 snaps. As another example, a ramped or keyed fit structure may be used. The different parts of the snap fit system are on either of the housing 32 or the ultrasound probe 12. In other embodiments, a thumb screw, latch or other structure is used. The structure is generally flush (e.g., less than 2 mm protrusion). In alternative embodiments, the releasable connection is formed by screws or other structures for which tools are used to connect and disconnect.

The housing 32 connects with the ultrasound probe 12 in any position relative to the ultrasound probe 12 and the needle guide 36. FIG. 2 shows one example where the housing 32 with the tracking sensor 34 releasably fits between the needle guide 36 and the ultrasound probe 12. FIG. 3 shows an example where the ultrasound probe 12 is sandwiched between the needle guide 36 and the housing 32. In other embodiments, one or both of the needle guide 36 and the housing 32 connect to the ultrasound probe 12 out of the plane of FIGS. 2 and 3.

The needle guide 36 is a plastic, resin, PEBAX®, or other material. The needle guide 36 may be disposable, such as made of a material that may not be sterilized since the needle guide 36 is to be discarded after a use with a patient. The same needle guide 36 is only used once and then discarded. To avoid fatigue for the sonographer, light weight material is preferred. As a result, plastic may be a preferred material. In alternative embodiments, the needle guide 36 is formed of one or more materials that may be sterilized or cleaned for use with multiple patients and/or have any weight.

The needle guide 36 has a hollow tube extending along the length axis. The hollow tube is sized to fit a biopsy needle. The hollow tube is positioned or oriented to assist in guiding the needle into the field of view of the array of the ultrasound probe 12. Other structures than a hollow tube may be provided.

The exterior of the needle guide 36 includes a surface for mating with the ultrasound probe 12, the housing 32, or both. The shape is the same or similar as the surfaces to which the needle guide 36 rests. The exterior also includes smooth, flat, or curved portions for contact with the patient. Structures that may tear, poke or harm a patient are avoided. When mated, the needle guide 36 in conjunction with the ultrasound probe 12 forms a smooth outer surface for contact with the patient.

The needle guide 36 is sized to guide a biopsy needle but otherwise limit expanding the diameter of the ultrasound system. For example, the needle guide 36 when mounted to the ultrasound probe 12 and the ultrasound probe 12 together have a greatest diameter of 20-30 mm. Other sizes may be provided.

The needle guide 36 is releasably connectable with the ultrasound probe 12. The connection is directly to the probe 12, through indirect connection to the housing 32 as connected to the probe 12, or both. The releasable connection is the same or different type of connection as used for the housing 32, such as a snap fit connector. In one embodiment, the needle guide 36 uses the snap fit at two or more locations to connect with the probe 12. In other embodiments, a different snap fit is provided. For example, the needle guide 36 has arms that wrap around part of the handle 26, cylinder part 30, and/or bulb part 28 to snap fit. In this way, the needle guide 36 may snap fit to the ultrasound probe 12 with the sterile sheath 38 between the probe 12 and needle guide 36 without puncturing the sterile sheath 38. The needle guide 36 connects to the ultrasound probe 12 outside of the sterile sheath 38 in order to guide the needle into, through, and beyond the needle guide 36.

The needle guide 36 connects to the ultrasound probe 12 independently of the housing 32. In the embodiment of FIG. 2, the needle guide 36 may connect with or without the housing 32 sandwiched between the needle guide 36 and the probe 12. The needle guide 36 and housing 32 may be selectively connected so that one, the other, or both may be connected for a given use.

The sterile sheath 38 is a flexible, sterile barrier or cover. The sterile sheath 38 is a plastic or other bag that fits over the portion of the probe 12 and housing 32 to be inserted into the patient. The sterile sheath 38 is of any thickness or material to prevent biological fouling of the probe 12 and housing 32. For biopsy, the sensor bracket or housing 32 is used inside the sterile sheath 38 (cover), and the needle guide 36 is placed over the covering sterile sheath 38. In alternative embodiments, the sterile sheath 38 is placed over the probe 12 but not the housing 32 of the sensor bracket.

Once the pieces are selected and connected together, the ultrasound probe 12 is inserted into the patient and used to scan with ultrasound in a way registered with MR data and/or to relatively determine the position of ultrasound scans during movement of the probe 12. Tracking signals from the tracking sensor 34 are used to determine the relative position of the ultrasound scans and/or position relative to the MR data. Once a lesion or other biopsy location is found from the imaging, the needle guide 36 assists in placement of the biopsy needle relative to the ultrasound scan during the biopsy. The physician uses the imaging to assist in locating and performing the biopsy of the lesion.

Figure 8:
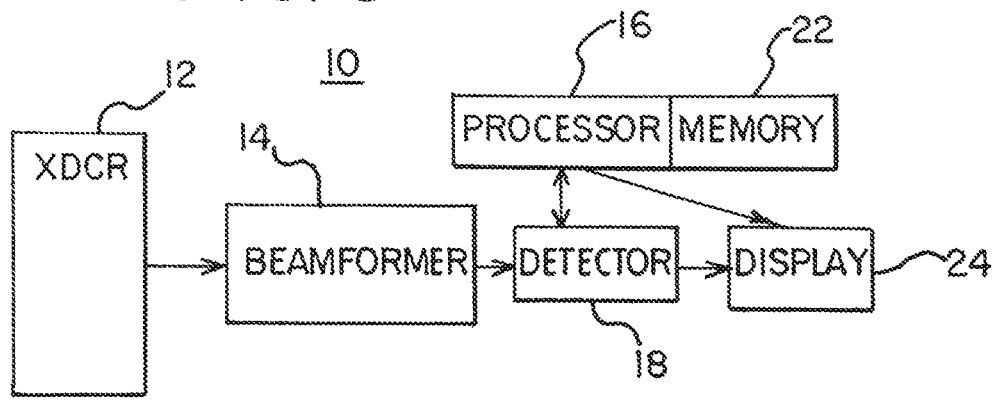
FIG. 8 is a block diagram of one embodiment of an ultrasound system for imaging with an ultrasound transducer probe.

FIG. 8 shows an ultrasound system used with the ultrasound probe 12. The system 10 may be used with a tracking sensor 34 and/or needle guide 36 while scanning a patient. The system 10 includes a transducer probe 12, a beamformer 14, a processor 16, a detector 18, a memory 22, and a display 24. Additional, different, or fewer components may be provided. For example, the system 10 includes a user interface. In one embodiment, the system 10 is a medical diagnostic ultrasound imaging system, and/or a computer with software that registers both multimodality images. In other embodiments, the processor 16 and/or memory 22 are part of a workstation or computer different or separate from an ultrasound imaging system. The workstation is adjacent to or remote from the ultrasound imaging system. In some embodiments, the transducer probe 12 is provided without other components.

The transducer probe 12 is a transducer array for medical diagnostic ultrasound imaging. The transducer probe 12 includes a probe housing and a transducer array. The array is a planar array, a curved array, a two-dimensional array, a radial array, an annular array, or other multidimensional array of transducer elements. The acoustic elements of the array are lead zirconate titanate (PZT) piezoelectric transduction material, ferroelectric relaxor or PVDF materials, capacitive membrane ultrasonic transducer (cMUT) materials, micro-machined membranes or beams, microelectromechanical devices, other piezoelectric material, or other means for acoustic-to-electric and/or electric-to-acoustic transduction.

The probe housing encases, surrounds most of, or is a protective frame work around the transducer array. The probe housing may include handles, grips, latches, connections, a transducer cable, or other components. Electronics may be provided within the probe housing, but the probe housing may be free of active (e.g., transistors, switches, or preamplifiers) electronics.

The transducer probe 12 has male or female mating components for snap fitting or other releasable connection with a housing of a tracking sensor and/or a needle guide. The different snap fit components may be selectively attached or unattached from the transducer probe 12.

The transducer probe 12 converts between electrical signals and acoustic energy for scanning a region of the patient's body. The region of the body scanned is a function of the type of transducer array and position of the transducer probe 12 relative to the patient. A linear aperture may scan a rectangular or square, planar region of the body. As another example, a curved linear aperture may scan a pie shaped region of the body. Scans conforming to other geometrical regions or shapes within the body may be used, such as Vector™ scans. The scans are of a two-dimensional plane, such as scanning at different azimuth angles relative to the aperture. Different planes or different segments of a plane may be scanned by moving the transducer array. To scan a volume, the transducer array is moved mechanically to scan different elevation spaced planes or electronically steers in multiple directions.

The beamformer 14 is configured by hardware and/or software. For example, focus tables are used to determine the delays or phases for steering acoustic beams. Pursuant to software control, the desired waveforms are generated for transmit operation, and the desired receive process is implemented.

In one embodiment, the beamformer 14 includes transmitters or waveform generators for generating electrical waveforms for each element of a transmit aperture. The waveforms are associated with phase and amplitude. The waveforms for a given transmit event may have the same or different phasing. The electrical waveforms are relatively weighted and delayed to form an acoustic beam with a desired phase and amplitude characteristic. For example, the transmit beamformer includes amplifiers, phase rotators, and/or controllers to generate sequential, steered pulses with the desired phase and amplitude in relation to other acoustic beams. Converging, diverging or planar beams may be used.

The beamformer 14 may include receive beamformers, such as delays, phase rotators, amplifiers, and/or adders for relatively delaying and summing received signals to form one or more receive beams with dynamic focusing. For example, using shared processing, separate processing, or combinations thereof, a plurality (e.g., tens or hundreds) of parallel receive beamformers are provided to form a respective plurality of receive beams in response to a given transmit beam. Alternatively, the beamformer 14 includes a processor for Fourier or other analysis of received signals to generate samples representing different spatial locations of the scanned region. In other embodiments, only one or a few (e.g., eight or fewer) receive beams are generated for each transmit beam.

The transducer probe 12 and beamformer 14 are connected together, such as the transmit beamformer channels connecting through coaxial cables to the transducer probe 12. The transducer probe 12 and beamformer 14 are configured to scan a planar region or a segment of a planar or volume region. The beamformer 14 is controlled or programmed to perform the scan. The beamformer parameters, such as relative delays and/or phasing for focus, apodization, beam amplitude, beam phase, frequency, or others, are set. The aperture for transmit and the aperture for receive on the transducer probe 12 is set. The beamformer 14 and transducer probe 12 are used to generate the waveforms for the aperture and convert the waveforms to acoustic energy for transmitting the beam. The beamformer 14 and transducer probe 12 are used to receive acoustic energy at the receive aperture, convert the acoustic energy to electrical energy, and beamform the received electrical signals.

Electric steering may be used to scan a plane. A volume scan may be performed using mechanical movement of the transducer array or further electric steering. Any pattern or distribution of scan lines and/or apertures may be used. Acoustic energy is transmitted in any of various now known or later developed scan patterns along each scan plane for acquiring data. The scan plane is then altered to another location in the volume by moving the transducer array. By moving the transducer array along the guide, or rotating the transducer along axis, a volume may be scanned. The volume is represented by data for a plurality of planes.

The detector 18 is configured to detect data output by the beamformer 14 and responsive to the transducer array. The detector 18 is an ultrasound detector. The detector is configured by hardware and/or software to detect from the beamformed and/or interpolated data. Any detection may be used, such as B-mode, Doppler or color flow mode, harmonic mode, contrast mode, or other now known or later developed modes. B-mode and some harmonic modes use single pulse scan techniques for detection. The intensity of the received signals in the frequency band of interest is calculated. Multiple pulse techniques, such as flow mode estimation of velocity or energy, may be used.

The detector 18 detects the response to the transmit beams for the scan of the volume. The spatial and/or temporal resolution of the detected data is based on the beamforming or scanning resolution. Detected data representing the plane or volume is provided.

The processor 16 is a rendering processor configured by hardware and/or software. The processor 16 is a general processor, control processor, application-specific integrated circuit, field-programmable gate array, graphics processing unit, digital circuit, analog circuit, digital signal processor, combinations thereof, or other now known or later developed device for generating a three-dimensional rendering of a volume scanned with different planes. The processor 16 is a single device or group of devices. For example, the processor 16 includes separate processors operating in parallel or sequence. As another example, the processor 16 includes a network of devices for distributed processing in parallel or sequence. In one embodiment, the processor 16 is a specific device for three-dimensional image rendering, such as a graphics processing unit, graphics card, or other device for rendering.

The processor 16 uses tracking signals from the tracking sensor 34. The signals are used to determine relative position of scan planes as the probe 12 is moved. The relative position may allow assembly of the planar scans into a volume representation. This representation may then be registered with a pre-operative scan, such as an MR scan. In other embodiments, the signals from the tracking sensor 34 are used to determine the position of the scan planes relative to the pre-operative scan volume.

The processor 16 may generate an image, such as a three-dimensional rendering, of the plane or volume being scanned. More than one image may be generated, such as one MR image with overlaid ultrasound information or as separate pre-operative and ultrasound images (e.g., 3D MR rendering with a 2D planar image from ultrasound). Image fusion uses the tracking from the tracking sensor 34. In other embodiments, image fusion is not provided. The processor 16 or detector 18 generates ultrasound images. The tracking signals are used for determining relative positions of scan planes or other usage without pre-operative data from another mode.

The processor 16, the detector 18, or a separate processor generates images from the volume scan and/or plane scan or other data output from the detector 18. For example, gray-scale and/or color coding is used to generate a B-mode, Doppler mode, or B-mode Doppler mode combination. Any image, such as a three-dimensional rendering, is output to the display 24.

The display 24 is a CRT, LCD, plasma, projector, printer, or other now known or later display device. The display 24 receives the image data from the processor 16 or other component and generates the image. A three-dimensional rendering, two-dimensional image, or other image is displayed.

The memory 22 is a tangible (non-transitory) computer readable storage medium, such as a cache, buffer, register, RAM, removable media, hard drive, optical storage device, or other computer readable storage media. The memory 22 is tangible by not being a signal, but a device. Computer readable storage media include various types of volatile and nonvolatile storage media. The memory 22 is accessible by the processor 16.

The memory 22 stores data representing instructions executable by the programmed processor 16, processor of the beamformer 14, and/or processor for scanning with ultrasound. The instructions for implementing the processes, methods and/or techniques discussed herein are provided on computer-readable storage media or memories. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system.

Figure 9:
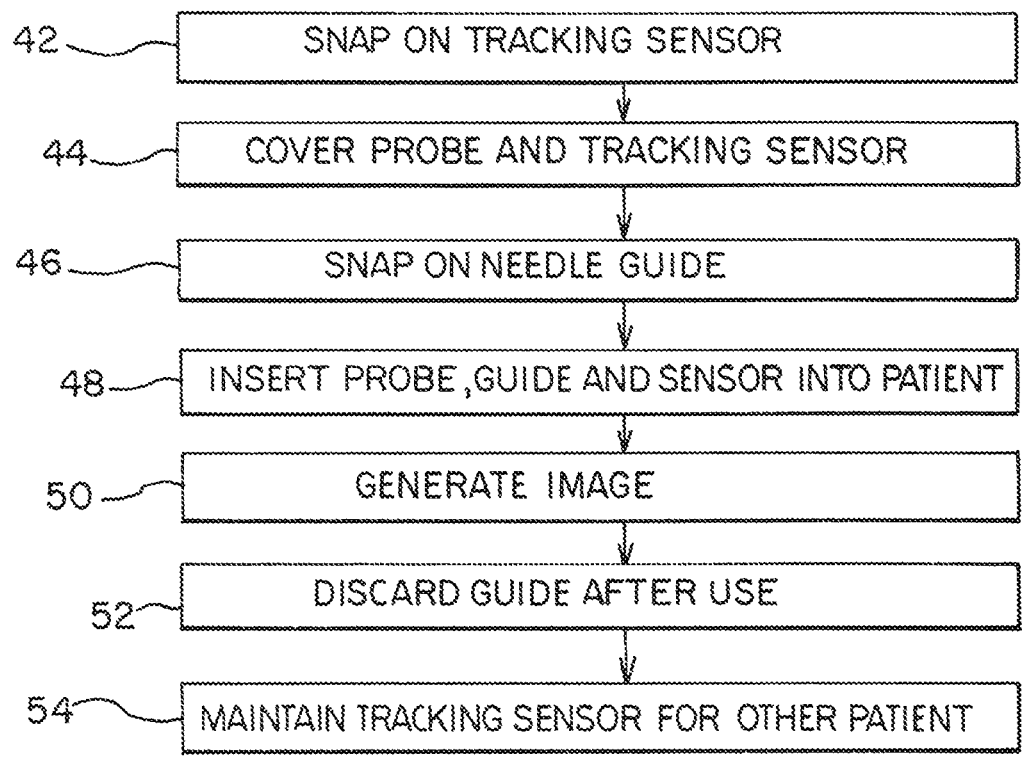
FIG. 9 is a flow chart diagram of one embodiment of a method for ultrasound imaging with snap fit tracking sensor and snap fit needle guide.

FIG. 9 is a flow chart diagram of one embodiment of a method for ultrasound imaging. The ultrasound transducer systems of FIGS. 2-4 and/or 7 are used with or without the imaging system of FIG. 8. In other embodiments, other probes and/or imaging systems are used.

In one embodiment, the method is for a prostate biopsy. In other embodiments, a biopsy of other organs or a non-biopsy procedure uses the method. The method is performed in the order shown or another order. For example, act 52 is performed after act 54. Additional, different, or fewer acts may be provided. For example, acts 44, 46, 50, 52, and/or 54 are not performed. For example, acts 42 and 46 are selectable (may or may not be performed as appropriate for a given ultrasound scan). As another example, acts for image fusion, spatial registration, and/or operating the ultrasound system are performed.

In act 42, a tracking sensor is snapped onto an exterior of an ultrasound transducer. A person, such as a sonographer, presses the tracking sensor and ultrasound transducer together. When aligned, the two pieces snap together. The snap fit holds them together under a certain amount of force. When the force is sufficient, the pieces may be separated, such as avoiding removal during use but allowing removal by the sonographer when done with a biopsy. The sensor bracket with the tracking sensor is removable if not needed.

The sensor bracket is an add-on component or part. The sensor bracket may be purchased separately or with the transducer. The sensor bracket may wear, so is replaceable. For example, a sensor bracket may be used for 6-10 biopsies and then replaced. Alternatively, the sensor bracket and tracking sensor may be used for more or fewer times before replacing or are never replaced. The sensor bracket may be used with different transducers, such as snap fitting with any of a same type and/or different types of transducer for use with any number of patients in sequence.

The tracking sensor is snapped or otherwise connected to the transducer so that the tracking sensor is adjacent to a distal end of the transducer. The connectors for the snap fitting align the sensor bracket with the tracking sensor so that the sensor is closer to the distal end of the transducer than to the handle.

In act 44, the transducer and the tracking sensor are covered. A sterile sheath is wrapped or slid over the connected transducer and sensor bracket. The sterile sheath is open on one end to slide over the transducer and sensor bracket and closed on the other end to form a sterile shield. The sterile sheath may be disposed of after use and prevents having to sterilize the transducer and tracking sensor as frequently. The transducer and sensor bracket may be sterilized, but the sheath allows multiple uses with different patients between sterilizing if desired.

In act 46, a needle guide, if desired, is snapped onto the exterior of the ultrasound transducer. The same type or different type of snap fit is used for the needle guide as the sensor bracket. The snap fit of the needle guide may hold the sensor bracket in place, such as due to sandwiching the sensor bracket. Alternatively, separate snap fitting is used.

The needle guide fits to a different part of the exterior of the transducer. Alternatively, the needle guide fits over the same part of the exterior.

The needle guide is connected outside of the sterile sheath. The needle guide is for a needle to interact with the patient, so is outside of the sterile field. The needle guide may be disposable or may be sterilized after each use.

The sensor bracket and the needle guide may be simultaneously connected to the transducer. Alternatively, the needle guide may be used without the sensor bracket or vise versa. For scanning for 3D fusion or 3D ultrasound imaging based on 2D planes, the sensor bracket may be used without the needle guide. For biopsy purposes, the needle guide may be used without the sensor bracket. Where fusion or 3D imaging is used to accurately guide the needle placement, both the sensor bracket and needle guide are snap fitted to the transducer.

In act 48, a portion of the transducer and the tracking sensor and/or needle guide are inserted into the patient. The transducer is inserted through a natural or operation-created hole in the patient for ultrasound scanning. The sensor is operable from within the patient for sensing position, change in position, orientation, and/or change in orientation. The insertion is for scanning from within the patient, sensing position of the array or scan region within the patient, and/or for guiding a biopsy needle with the guide partly within the patient.

The inserted transducer and corresponding connected pieces may be repositioned. The transducer is moved during imaging to locate a lesion or part to be biopsied. The tracking information is used to guide, locate, and/or fuse ultrasound information with pre-operative information to assist in biopsy.

In act 50, an image is generated. The transducer, while inserted in the patient, is used to scan the patient with ultrasound. The resulting scan data is used to generate an ultrasound image. The ultrasound image may or may not be fused with data or an image from a different modality (e.g., pre-operative MR data). The image is a two-dimensional image representing a plane, or the image is a three-dimensional rendering.

The image is generated as a function of the tracking data from the tracking sensor while also within the patient. The tracking data may be used to determine the position of the scan plane or region relative to a pre-operative volume. Alternatively or additionally, the tracking data is used to determine relative positioning of scan planes to create a data set representing a three-dimensional volume. The volume data is then used for rendering an image. Free-hand three-dimensional fusion imaging may be provided, such as allowing user-based movement (e.g., translation and/or rotation) of the transducer to scan a volume one plane at a time. The planes are spatially assembled based on the tracking data. The resulting volume data may be fused with volumes of other modalities.

In other embodiments, the needle guide may be used with or without the tracking sensor. Once the imaging indicates the lesion to be biopsied within the scan plan, the needle is inserted into the patient. The needle guide directs the needle along the scan plane or to the scan plane. The needle is directed to the lesion using feedback (e.g., imaging coordinates) from the ultrasound imaging. For example, the patient is scanned, the resulting image is fused with pre-operative image data, a biopsy is performed using the imaging, and the location of the biopsy relative to the images is recorded for future use with histopathology results.

In act 52, the needle guide is discarded after use. Since the needle guide may be made out of inexpensive materials, such as PEBAX or plastic, and is exposed when inserted into the patient, the needle guide may be a disposable part discarded after a single use. In alternative embodiments, the needle guide may be sterilized and reused, but only a limited number of times. After the limited number is reached, the needle guide is discarded.

In act 54, the tracking sensor is maintained. The tracking sensor may be relatively expensive, so the sensor bracket is protected by the sterile barrier and/or constructed of more durable and sterilizable material. The tracking sensor is used until inoperable. Alternatively, limited number of uses may be provided. The same sensor bracket is used with different patients. Due to the releasable connection, the same sensor bracket may be used with different transducers and/or patients.

While the invention has been described above by reference to various embodiments, it should be understood that many changes and modifications can be made without departing from the scope of the invention. The above embodiments are examples. It is therefore intended that the foregoing detailed description be understood as an illustration of the presently preferred embodiments of the invention, and not as a definition of the invention. It is only the following claims, including all equivalents, that are intended to define the scope of this invention.

What is claimed is:

1. An integrated needle guide tracking system comprising:
an endocavity probe having an endocavity ultrasound transducer, the endocavity probe having a distal tip opposite a handle shaped for being held by a person, a bulb of the distal tip having a greater diameter in axial cross-section than an arm connecting the bulb to the handle, the bulb, the arm, and the handle formed as an integrated housing;
a tracking sensor positioned on the bulb of the distal tip such that the sensor is insertable within a patient cavity with the distal tip, the tracking sensor comprises a sensor housing releasably connectable with the endocavity ultrasound transducer; and
a needle guide connected with the endocavity ultrasound transducer, wherein the needle guide is releasably connected with the endocavity ultrasound transducer;
the sensor housing and/or the needle guide releasably connected using a tab or keyed structure configured to connect and releasably connect without a tool.

2. The integrated needle guide tracking system of claim 1 wherein the endocavity ultrasound transducer comprises a housing with an acoustic window at the distal tip and a transducer array adjacent to the acoustic window within the housing.

3. The integrated needle guide tracking system of claim 1 wherein the tracking sensor comprises a magnetic position sensor.

4. The integrated needle guide tracking system of claim 1 wherein the tracking sensor comprises an elongated housing shaped to match a contour of the endocavity ultrasound transducer, where the tracking sensor is at an end of the elongated housing.

5. The integrated needle guide tracking system of claim 1 wherein the housing is releasably connectable with a releasable snap fit.

6. The integrated needle guide tracking system of claim 1 wherein the needle guide comprises a hollow tube.

7. The integrated needle guide tracking system of claim 1 wherein the needle guide is releasably connected to the endocavity ultrasound transducer with a snap fit.

8. The integrated needle guide tracking system of claim 1 wherein the tracking sensor is shaped to releasably fit between the needle guide and the endocavity ultrasound transducer.

9. The integrated needle guide tracking system of claim 1 further comprising a sterile barrier covering the endocavity ultrasound transducer and the tracking sensor, the needle guide being connected to the endocavity ultrasound transducer outside of the sterile barrier.

10. The integrated needle guide tracking system of claim 1 wherein the needle guide is disposable.

11. The integrated needle guide tracking system of claim 1 wherein the endocavity ultrasound transducer comprises the bulb at the distal end connected with an elongated cylindrical shape to the handle, the tracking sensor comprising an elongated housing connectable to the bulb and the elongated cylindrical housing or the handle such that a greatest diameter of the endocavity ultrasound transducer with the elongated housing is equal to the greatest diameter of the bulb.

12. An ultrasound transducer system comprising:
an endocavity probe comprising an ultrasound probe, the endocavity probe having a portion shaped for insertion into a cavity of a patient, the portion including a bulb having a greater diameter in axial cross-section than an arm connecting the bulb to a handle, the bulb, the arm, and the handle formed as an integrated housing;
a housing separate from the ultrasound probe, the housing releasably connectable with the portion using a tab or keyed structure configured to releasably connect without a tool; and
a tracking sensor embedded in the housing so that the tracking sensor is positioned on the bulb when the housing is connected to the portion using the tab or keyed structure; and
a needle guide releasably connected with the endocavity probe.

13. The ultrasound transducer system of claim 12 wherein the tracking sensor comprise a magnetic position sensor positioned in the housing to be closer to a distal part of the portion than a proximal part of the portion.

14. The ultrasound transducer system of claim 12 wherein the ultrasound probe is sized and shaped for insertion into a rectum, esophagus, or vagina.

15. The ultrasound transducer system of claim 12 wherein the housing is releasably connectable by a snap fit.

16. The ultrasound transducer system of claim 12 further comprising wherein the needle guide is releasably connectable with the ultrasound endocavity probe by another tab or keyed structure.

17. A method for ultrasound imaging, the method comprising:
snapping a tracking sensor onto an exterior of an endocavity probe of an ultrasound transducer, the snapping being with a releasable snap fit formed by one or more tabs so that the tracking sensor is positioned on a distal end part of the ultrasound transducer having an integrated housing comprising a bulb at the distal end connected to a handle by an arm, the bulb having a greater diameter in axial cross-section than the arm, the tracking sensor being positioned by the bulb;
snapping a needle guide onto an exterior of the ultrasound transducer, the snapping of the needle guide comprising snapping without a tool;

covering the tracking sensor and ultrasound transducer with a sterile sheath;

inserting a portion, including the distal end part, of the ultrasound transducer and the tracking sensor into a patient; and generating an image from scan data acquired with the ultrasound transducer while inserted in the patient and as a function of tracking data from the tracking sensor while inserted in the patient.

18. The method of claim 17 further comprising:
wherein snapping the needle guide onto the exterior of the ultrasound transducer comprising snapping the needle guide outside of the sterile sheath with other tabs;
wherein inserting comprises inserting the portion, the tracking sensor, and a part of the needle guide into the patient.

19. The method of claim 18 further comprising:
discarding the needle guide after use for the patient; and
maintaining the tracking sensor for use with a different patient.

* * * * *